(12) United States Patent
Xiao et al.

(10) Patent No.: US 7,926,133 B2
(45) Date of Patent: Apr. 19, 2011

(54) MUSICAL PILLOW

(75) Inventors: Shi-Xin Xiao, Shenzhen (CN);
Chung-Yuan Chen, Taipei Hsien (TW);
Long-Fong Chen, Taipei Hsien (TW);
Ji-Ping Wu, Shenzhen (CN); Shi-Bin Li, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 0 days.

(21) Appl. No.: 12/508,520

(22) Filed: Jul. 23, 2009

(65) Prior Publication Data
US 2010/0275378 A1 Nov. 4, 2010

(30) Foreign Application Priority Data
Apr. 30, 2009 (CN) .......................... 2009 1 0302021

(51) Int. Cl.
*A47G 9/10* (2006.01)

(52) U.S. Cl. ..................................... 5/639; 5/904; 5/636
(58) Field of Classification Search .............. 5/622, 630, 5/636–637, 904, 639
See application file for complete search history.

(56) References Cited

U.S. PATENT DOCUMENTS

| | | | | |
|---|---|---|---|---|
| 6,098,220 A | * | 8/2000 | Momma | 5/636 |
| 6,640,367 B2 | * | 11/2003 | Hsia | 5/640 |

* cited by examiner

*Primary Examiner* — Frederick Conley
(74) *Attorney, Agent, or Firm* — Frank R. Niranjan

(57) ABSTRACT

The present invention relates to a musical pillow. The music pillow includes a body, a pillow core defining a first receiving cavity corresponding to a users' head, and a music player device. The body includes a first base, and two sidewalls extending from two opposite sides of the first base. Two free ends of the two sidewalls face each other to define a body opening therebetween. The first base and the two sidewalls cooperatively define a receiving space. The pillow core is received in the receiving space, while the first receiving cavity is communicated with the body opening. The music player device includes two speakers positioned on the sidewalls respectively and a playing unit positioned in the first base. The speakers are electrically connected to the playing unit.

9 Claims, 4 Drawing Sheets

MUSICAL PILLOW

BACKGROUND

1. Technical Field

The present disclosure relates to pillows, and particularly, to a musical pillow.

2. Description of Related Art

Generally, pillows are shaped to accommodate users' head and neck. The shape of the pillow is changed according to the shape and size of users' head and neck to provide a comfortable feeling and allow users to rest peacefully. However, if a pillow can provide music to users, it will make users more comfortable and further improve the sleeping quality. Hence, adding a function of playing music in pillows is of great importance in pillow design.

DETAILED DESCRIPTION

Figure 1:
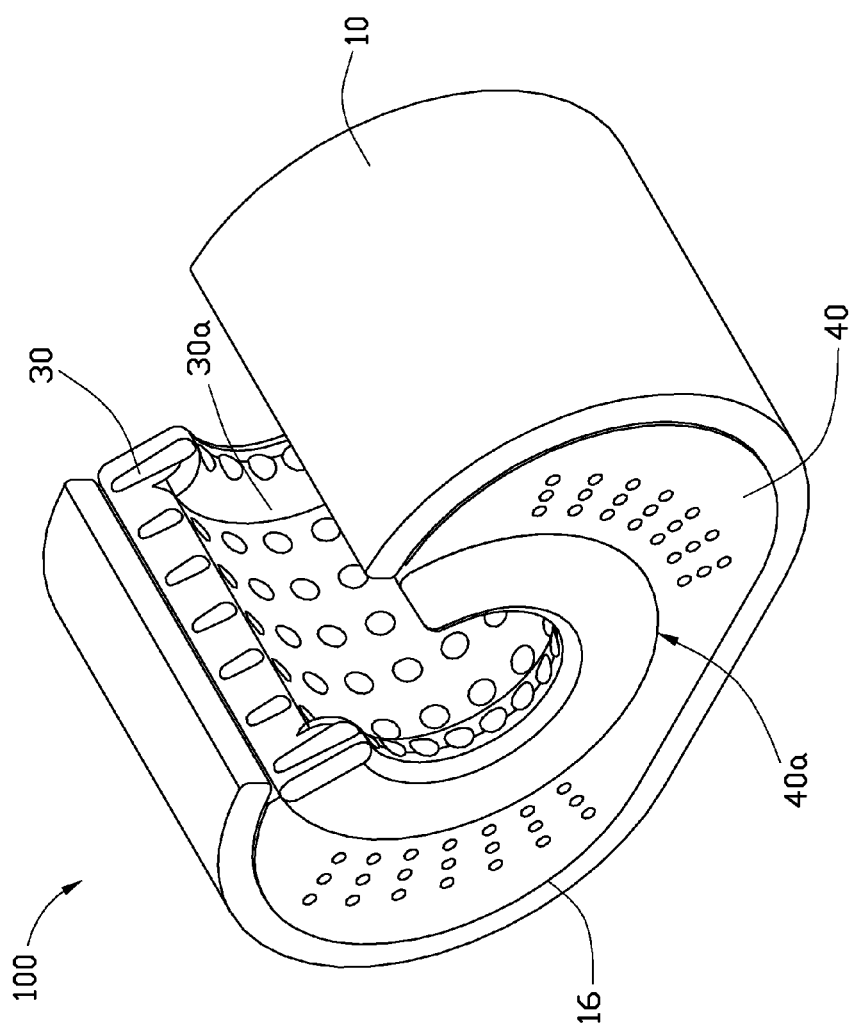
FIG. 1 is a schematic isometric view of a musical pillow, according to an exemplary embodiment.
Figure 2:
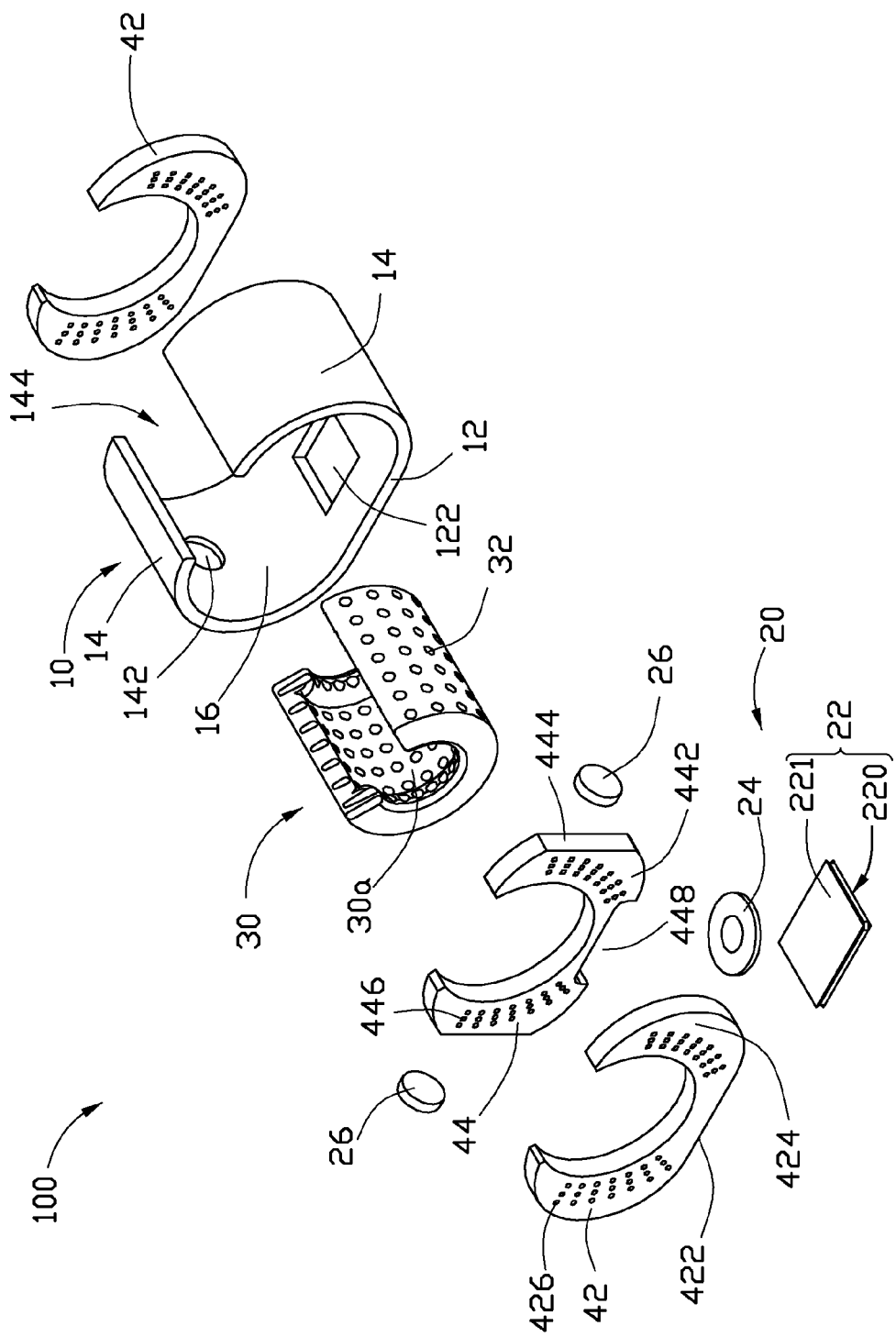
FIG. 2 is an exploded view of the musical pillow of FIG. 1.

Referring to FIGS. 1 and 2, a musical pillow 100, according to an exemplary embodiment, includes a body 10, a music player device 20, a pillow core 30, and a supporting assembly 40.

The body 10 includes a first base 12 and two sidewalls 14 extending from opposite sides of the first base 12 correspondingly. A base opening 122 is defined in the first base 12. Each sidewall 14 defines a receiving groove 142. Two distal ends of the two sidewalls 14 face each other to define a body opening 144. The first base 12 and the two sidewalls 14 cooperatively define a receiving space 16.

Figure 3:
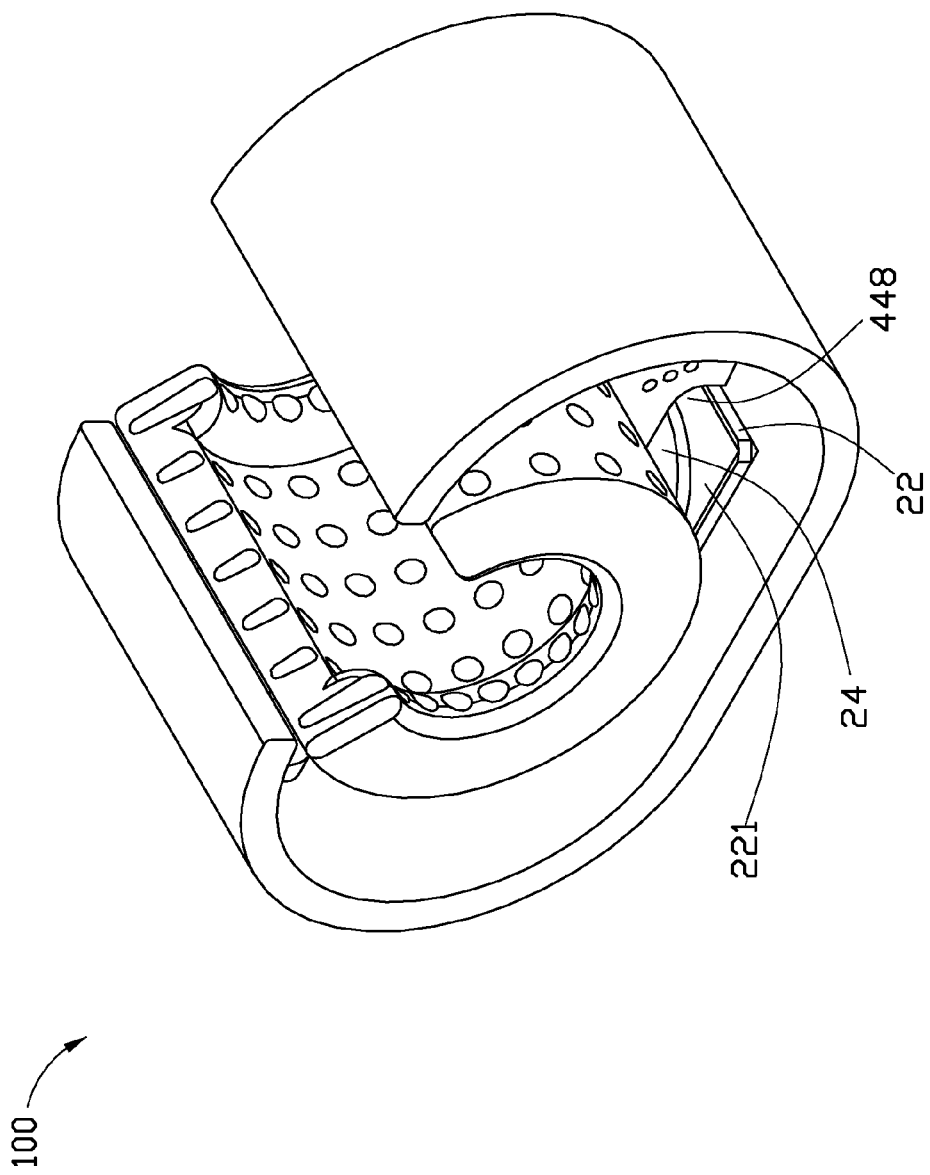
FIG. 3 is a partially, schematic isometric view of the musical pillow of FIG. 1.
Figure 4:
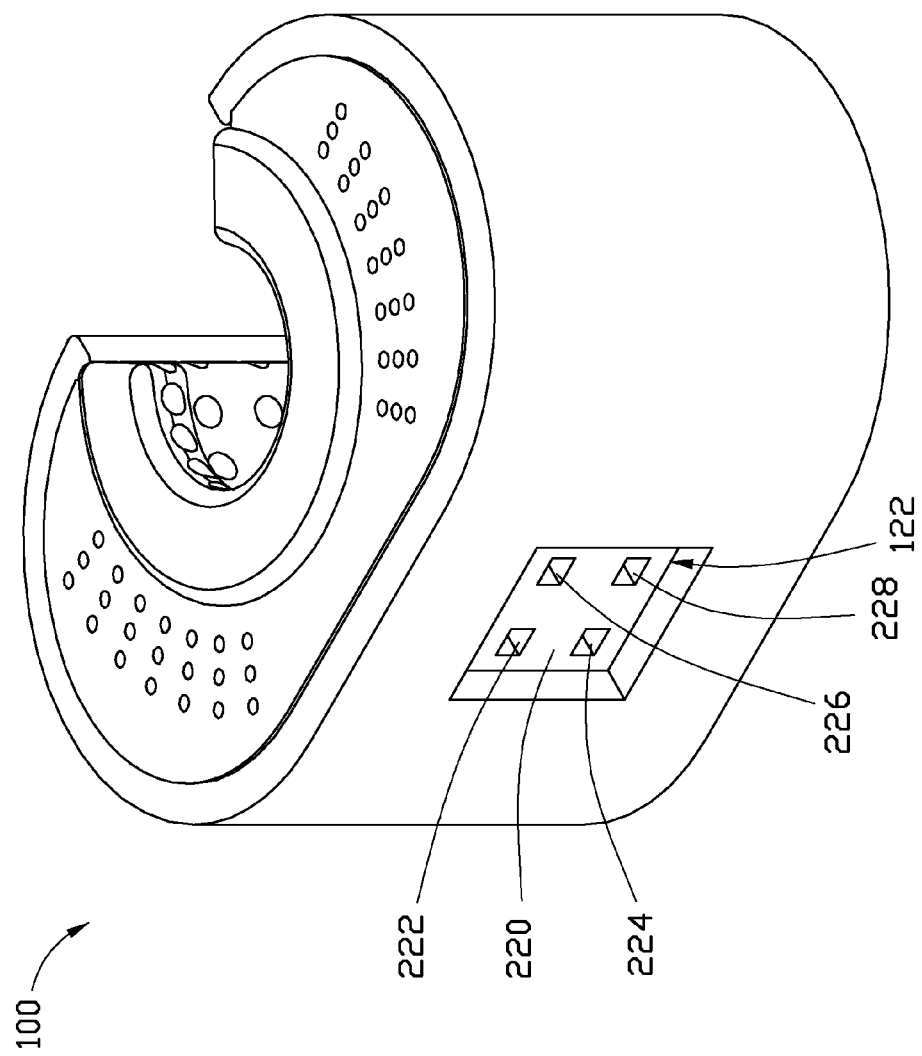
FIG. 4 is similar to the FIG. 1, but viewing from another angle.

Further referring to FIGS. 3 and 4, the music player device 20 includes a playing unit 22, a bass speaker 24, and two treble speakers 26.

The playing unit 22 includes a lower surface 220 and an upper surface 221 opposite to the lower surface 220. The playing unit 22 is fixed to the first base 12 by glue to cover the lower surface 220 over the base opening 122. The playing unit 22 further includes a volume adjuster 222, a power supply socket 224, a memory card socket 226, and a controller 228. The volume adjuster 222, the power supply socket 224, the memory card socket 226, and the controller 228 are positioned on the lower surface 220, exposed at the base opening 122.

The volume adjuster 222 is configured for adjusting the volume of the playing unit 22. The power supply socket 224 is configured for electrically connecting an external power source (not shown) to the music player device 20. The memory card socket 226 is configured for coupling with a memory card (not shown) that stores a plurality of songs. The controller 228 is configured for activating the playing unit 22 and selecting a song to reproduce from the plurality of songs.

The bass speaker 24 is fixed to the upper surface 221 of the playing unit 22 by glue. The two treble speakers 26 are fixed in the two receiving grooves 142 by glue, correspondingly. The bass speaker 24 and the treble speakers 26 are electrically connected to the playing unit 22 by wires.

In other exemplary embodiment, the playing unit 22 may be fixed to the first base 12 by a screw joint. The bass speaker 24 may be fixed to the upper surface 221 by a screw joint. The two treble speakers 26 may be fixed in the two receiving grooves 142 by a screw joint.

A first receiving cavity 30a to rest/place one's head is defined in the pillow core 30. A plurality of first through holes 32 are defined in the pillow core 30 and configured for transmitting sound.

The supporting assembly 40 defines a second receiving cavity 40a for receiving the pillow core 30. The supporting assembly 40 is embedded in the receiving space 16. The pillow core 30 is received in the second receiving cavity 40a, and the first receiving cavity 30a communicates with the body opening 144. The supporting assembly 40 includes two opposite outer supporting plates 42 and a middle supporting plate 44 between the two outer supporting plates 42.

Each outer supporting plate 42 is embedded in the receiving space 16, and includes a second base 422 and two first arms 424 extending from opposite sides of the second base 422. A plurality of second through holes 426 are defined in each outer supporting plate 42 and configured for transmitting sound. The second base 422 abuts the first base 12, and the two first arms 424 abut the two sidewalls 14, correspondingly.

The middle supporting plate 44 includes a third base 442 and two second arms 444 extending from opposite sides of the third base 442. A plurality of third through holes 446 corresponding to the second through holes 426 are defined in the middle supporting plate 44 and configured for transmitting sound. A cutout 448 is defined in the third base 442. The middle supporting plate 44 is embedded in the receiving space 16. The third base 442 abuts the first base 12. The playing unit 22 and the bass speaker 24 extend through the cutout 448. The two second arms 444 are apart from the two sidewalls 14 for receiving the two treble speakers 26, correspondingly.

Before the musical pillow 100 plays music, an external power source (not shown) is electrically connected to the playing unit 22 through the power supply socket 224 and a memory card (not shown) is coupled with the memory card socket 226. When the playing unit 22 is activated and a favorite song is selected through the controller 228, a person resting one's head in the first receiving cavity 30a can listen to one's favorite song from the bass speaker 24 and the two treble speakers 26. This makes one more comfortable and further improves one's sleeping quality.

It is to be understood, however, that even though numerous characteristics and advantages of the present embodiments have been positioned fourth in the foregoing description, together with details of the structures and functions of the embodiments, the disclosure is illustrative only, and changes may be made in details, especially in matters of shape, size, and arrangement of parts within the principles of the invention to the full extent indicated by the broad general meaning of the terms in which the appended claims are expressed.

What is claimed is:

1. A musical pillow comprising:
   a body comprising a first base and two sidewalls extending from opposite sides of the first base, two distal ends of the two sidewalls facing each other to define a body opening facing the first base, the first base and the two sidewalls cooperatively defining a receiving space;
   a pillow core defining a first receiving cavity for receiving a user's head, the pillow core embedded in the receiving space, and the first receiving cavity communicated with the body opening;

a supporting assembly defining a second receiving cavity for receiving the pillow core and comprising two opposite outer supporting plates, each supporting plate embedded in the receiving space and comprising a second base and two first arms extending from opposite sides of the second base, the second base abutting the first base, the first arms abutting the sidewalls respectively; and a music player device comprising at least one speaker positioned on the sidewall and a playing unit fixed in the first base between the two outer supporting plates, the at least one speaker electrically connected to the playing unit.

2. The musical pillow as claimed in claim 1, wherein a base opening is defined in the first base; and the playing unit is fixed to the first base and covers the base opening.

3. The musical pillow as claimed in claim 2, wherein the at least one speaker comprises two speakers, each sidewall defines a receiving groove, and each speaker is fixed in the receiving groove respectively.

4. The musical pillow as claimed in claim 3, wherein each speaker is fixed in the receiving groove by glue or by a screw joint.

5. The musical pillow as claimed in claim 3, wherein the supporting assembly further comprises a middle supporting plate between the two outer supporting plates, the middle supporting plate comprises a third base and two second arms extending from opposite sides of the third base; a cutout is defined in the third base; the middle supporting plate is embedded in the receiving space; the third base abuts the first base, while the playing unit passes through the cutout;

and the two second arms are apart from the two sidewalls facing the two speakers, respectively.

6. The musical pillow as claimed in claim 5, wherein a plurality of second through holes are defined in each outer supporting plate and configured for transmitting sound; and a plurality of third through holes corresponding to the second through holes are defined in the middle supporting plate and configured for transmitting sound.

7. The musical pillow as claimed in claim 5, wherein the two speakers are treble speakers, the music player device further comprises a bass speaker, the bass speaker is fixed to the playing unit and passes through the cutout, and the bass speaker and the treble speakers are electrically connected to the playing unit.

8. The musical pillow as claimed in claim 7, wherein the playing unit comprises a lower surface and an upper surface opposite to the lower surface; the lower surface faces the base opening;

the playing unit further comprises a volume adjuster, a power supply socket, a memory card socket, and a controller; and the volume adjuster, the power supply socket, the memory card socket, and the controller are positioned on the lower surface and exposed at the base opening.

9. The musical pillow as claimed in claim 1, wherein a plurality of first through holes are defined in the pillow core and configured for transmitting sound.

* * * * *